US007399746B2

(12) United States Patent
Congote (10) Patent No.: US 7,399,746 B2
(45) Date of Patent: Jul. 15, 2008

(54) AGENTS FOR WOUND HEALING (75) Inventor: Luis Fernando Congote, Montreal (CA)

(73) Assignee: McGill University, Montreal, Quebec (CA)

( * ) Notice: Subject to any disclaimer, the term of this patent is extended or adjusted under 35 U.S.C. 154(b) by 388 days.

(21) Appl. No.: 11/244,925

(22) Filed: Oct. 6, 2005

(65) Prior Publication Data
US 2006/0073132 A1    Apr. 6, 2006

Related U.S. Application Data

(60) Provisional application No. 60/616,293, filed on Oct. 6, 2004.

(51) Int. Cl.
*A61K 38/16* (2006.01)
*A61K 38/00* (2006.01)

(52) U.S. Cl. ............................................ 514/12; 514/2

(58) Field of Classification Search ........................ None
See application file for complete search history.

(56) References Cited

U.S. PATENT DOCUMENTS

| 5,093,316 | A | * | 3/1992 | Lezdey et al. | .................. | 514/8 |
| 5,190,917 | A | * | 3/1993 | Lezdey et al. | .................. | 514/12 |
| 5,412,073 | A | * | 5/1995 | Kalsheker | .................. | 530/350 |
| 6,150,332 | A | * | 11/2000 | Wright et al. | .................. | 514/16 |
| 6,638,909 | B1 | * | 10/2003 | Grady et al. | .................. | 514/8 |

FOREIGN PATENT DOCUMENTS

GB      2318732      *   6/1998

OTHER PUBLICATIONS

P. Brand et al. (2003). "Peripheral deposition of alpha1-protease inhibitor using commercial inhalation devices," The European Respiratory Journal vol. 22, pp. 263-267.*
M.D. Wewers et al. (1987). "Replacement therapy for alpha1-antitrypsin deficiency associated with emphysema," New England Journal of Medicine vol. 316, pp. 1055-1062.*
C. Sandoval et al. (2003). "The fusion of IGF I with stromal cell-derived factor I or alpha1 proteinase inhibitor alters their mitogenic or chemotactic activities which keeping their ability to inhibit HIV-1-gp120 binding," Biochemical Pharmacology vol. 65, pp. 2055-2063.*
C. Sandoval et al. (2002). "Enhanced proliferative effects of a caculovirus-produced fusion protein of insulin-like growth factor and alpha1-proteinase inhibitor and improved anti-elastase activity of the inhibitor with glutamate at position 351," Protein Engineering vol. 15, pp. 413-418.*
Congote et al., The C-terminal 26-residue peptide of serpin A1 stimulates proliferation of breast and liver cancer cells:role of protein kinase C and CD47, 2004, FEBS letters, v576, 343-347.*

Catanese et al., Oppossum serum alpha-1 proteinase inhibitor, 1993, Biochemistry, v32, 509-515.*
Merck on-line manual (www.merck.com/mmhe) 'alpha-1 antitrypsin deficiency entry accessed 2007, 2 pages.*
Crisp et al., "Roles of the Heparin and Low Density Lipid Receptor-related Protein-binding Sites of Protease Nexin 1 (PN1) in Urokinase-PN1 Complex Catabolism", J. Biol. Chem. 2000.
Cullen et al., "Mechanism of action of PROMOGRAN, a protease modulating matrix, for the treatment of diabetic foot ulcers", Wound Repair and Regeneration 2002 10(1):16-25.
Dabbagh et al., "Alpha-1-Antitrypsin Stimulates Fibroblast Proliferation and Procollagen Production and Activates Classical MAP Kinase Signalling Pathways", J. Cell. Physiol. 2001 186(1):73-81.
Galiano et al., "Interaction between the Insulin-like Growth Factor Family and the Integrin Receptor Family in Tissue Repair Processes", J. Clin. Invest. 1996 98(11):2462-2668.
Johansson et al., "Identification of hydrophobic fragments of $\alpha_1$-antitrypsin and C1 and protease inhibitor in human bile, plasma and spleen", FEBS 1992 299(2):146-148.
Ledoux-Corbusier et al., "$\alpha_1$-Antitrypsin Deficiency and Skin Abnormalities", J. Cutan. Pathol. 1975 2(1):25-29.
Loots et al., "Fibroblasts derived from chronic diabetic ulcers differ in their response to stimulation with EGF, IGF-1, bFGF and PDGF-AB compared to controls", Eur. J. Cell Biol. 2002 81(3):153-160.
Nwomeh et al., "Physiology of the Chronic Wound", Clinics in Plastic Surgery 1998 25(3):341-356.
Rao et al., "α1-Antitrypsin Is Degraded and Non-Functional in Chronic Wounds But Intact and Functional in Acute Wounds:The Inhibitor Protects Fibronectin from Degradation by Chronic Wound Fluid Enzymes", J. Invest. Dermatol. 1995 105(4):572-578.
Sandoval et al., "Enhanced proliferative effects of a baculovirus-produced fusion protein of insulin-like growth factor and $\alpha_1$-proteinase inhibitor and improved anti-elastase activity of the inhibitor with glutamate at position 351", Protein Engineering 2002 15(5):413418.
Sandoval et al., "The fusion of IGF I with stromal cell-derived factor I or α1 proteinase inhibitor alters their mitogenic or chemotactic activities while keeping their ability to inhibit HIV-1-gp120 binding", Biochemical Pharmacology 2003 65:2055-2063.
Schwede et al., "Swiss-Model:an automated protein homology-modeling server", Nucleic Acids Research 2003 31(13):3381-3385.
Stockley et al., "Effect of Alpha-1-Proteinase Inhibitor on Neutrophil Chemotaxis", Am. J. Respir. Cell Mol. Biol. 1990 2:163-170.
Wachter et al., "Treatment of atopic dermatitis with alpha$_1$-proteinase inhibitor", Annals of Allergy 1992 69(5):407414.

* cited by examiner

*Primary Examiner*—Anish Gupta
*Assistant Examiner*—Ronald T Niebauer
(74) *Attorney, Agent, or Firm*—Licata & Tyrrell PC (57) ABSTRACT

The present invention relates to pharmaceutical compositions containing fragments of alpha-1 proteinase inhibitor (API) or chimeric proteins of API and insulin-like growth factor for use in stimulating wound healing.

4 Claims, 4 Drawing Sheets

AGENTS FOR WOUND HEALING

This application claims the benefit of priority from U.S. provisional patent application Ser. No. 60/616,293, filed Oct. 6, 2004, the contents of which are incorporated herein by reference.

BACKGROUND OF THE INVENTION

It is widely recognized that in the United States almost 8 million people per year have burns or suffer from chronic, non-healing wounds (Singer & Clark (1999) *N. Engl. J. Med.* 341(10):738-746). Chronic wounds invariably occur in individuals with underlying disease and impaired wound healing is a hallmark of diabetic complications. Chronic wounds generally fall into three principal categories: venous stasis ulcers, diabetic ulcers and pressure ulcers. While the prevalence of these conditions vary, it is estimated that as many as 12 million people are afflicted with all forms of chronic wounds in the principal industrialized markets.

Approximately 800,000 diabetic foot ulcers are treated in the United States each year, of which 30% do not respond to standard care. Given that 15-20% of patients with foot ulcers will require amputation, these data underscore the medical benefit and cost saving that may be achieved through emerging technologies and therapies addressing chronic wound repair as provided by this invention.

Wound care and healing technology is evolving rapidly with new product offerings that respond to medical needs in both the acute and chronic wound management setting. According to the most recent National Health Interview Survey (NHIS), the incidence of burn injury causing wound stands at 4.2/10,000 or about 1.2 million annually. While severe wounds attributable to burns are significant, a staggering population of greater than 6 million people is afflicted with chronic ulcerations resulting from dermatological conditions and chronic ulcerations secondary to diabetes, immunosuppression and immobilization. Both acute and chronic wounds represent a major health problem, and a new generation of novel agents for wound healing are based on topical growth factors and protease inhibition therapy (Nwomeh, et al. (1998) *Clin. Plast. Surg.* 25:341-56).

Wound healing is dynamic process. The wound environment is variable depending on the health status of the individual and the underlying pathology. Knowledge of the physiology of the normal wound healing cycle through the phases of hemostasis, inflammation, granulation and maturation provides a framework for developing novel single or combination therapies.

In animal models of the disease, certain recombinant growth factors only partially enhance wound repair associated with diabetic state, however this efficacy may be increased using growth factor combinations such as TGF beta and basic FGF or TGF beta and PDGF. Consistent with this finding is the observation that combination of certain growth factors in fibroblasts cultured from human diabetic ulcers reproducibly cause a greater mitogenic response compared to any agent alone (Loot, et al. (2002) *Eur. J. Cell Biol.* 81(3): 153-160). Moreover, topical applications of IGFs promote wound healing, in particular in association with IGF-binding proteins (Galiano, et al. (1996) *J. Clin. Invest.* 98(11):2462-8). Poor chronic wound healing in diabetic rats is associated with increased proteolytic enzymes, reduced IGF levels and destruction of IGF-binding proteins (Cechowska-Pasko, et al. (1996) *Acta Biochimica Polonica* 43(3):557-65). It is generally accepted that intervening parameters such as prolific proteolytic activity in the wound are deleterious to proper healing by degrading de novo granulation tissue and local growth factors and cytokines. Common proteases in the wound microenvironment are neutrophil elastase, matrix metalloproteases and plasmin (Cullen, et al. (2002) *Wound Repair Regen.* 10(1):16-25).

In burn-wound fluids, elastase from neutrophils is responsible for fibronectin degradation (Grinnell & Zhu (1994) *J. Invest. Dermatol.* 103(2):155-61). Neutrophil elastase activity is ten- to forty-fold higher in fluids from chronic wounds as compared with fluids from acute wounds. API, also known as alpha-1-antitrypsin, the major physiological inhibitor of neutrophil elastase, is conspicuously absent and not functional in chronic wounds (Rao, et al. (1995) *J. Invest. Dermatol.* 105(4):572-8). Moreover, in a case report of a patient with complete API deficiency, major skin abnormalities were observed (Ledoux-Corbusier & Achten (1975) *J. Cutan. Pathol.* 2(1):25-9), compatible with a phenotype of uncontrolled elastase activity. Furthermore, in a pilot study, six patients with atopic dermatitis, who had failed to respond to high potency topical steroids, showed a remarkable improvement in tissue healing after topical application of API (Wachter & Lezdey (1992) *Ann. Allergy* 69(5):407-14).

Site-directed mutagenesis of the anti-elastase API active site suggests that the growth-promoting activity of API may be governed by a sequence that is distinct from its enzyme inhibitory domain (Sandoval, et al. (2002) *Protein Eng.* 15:413-8). The endogenous 36 amino acid C-terminal fragment of API (C36) is produced after proteolytic cleavage of the inhibitor. This is the only section of API (independent of the active site inhibitory loop) known to have biological activity. This peptide, which has been isolated from spleen and bile (Johansson, et al. (1992) *FEBS Lett.* 299(2):146-8) and shown to have chemotactic activity (Stockley, et al. (1990) *Am. J. Respir. Cell Mol. Biol.* 2(2):163-70).

SUMMARY OF THE INVENTION

The present invention is a method for stimulating wound healing. The method involves administering an effective amount of at least a portion of an alpha-1 proteinase inhibitor so that wound healing is stimulated. In particular embodiments, at least a portion of an insulin-like growth factor I polypeptide is operatively linked to the portion of the alpha-1 proteinase inhibitor. In other embodiments, the alpha-1 proteinase inhibitor contains glutamine for methionine at amino acid residue 351 and leucine for methionine at amino acid residue 358. In still other embodiments, the alpha-1 proteinase inhibitor encompasses the carboxy-terminal 26 amino acid residues of the inhibitor.

The present invention is also a method for treating a disease or condition associated with the liver. This method involves administering an effective amount of at least a portion of an alpha-1 proteinase inhibitor so that a disease or condition associated with the liver is treated. Particular embodiments of this method embrace the use of an alpha-1 proteinase inhibitor composed of the carboxy-terminal 26 amino acid residues of said inhibitor.

The present invention is also a pharmaceutical composition composed of at least a portion of an alpha-1 proteinase inhibitor or a portion of an alpha-1 proteinase inhibitor operatively linked to at least a portion of an insulin-like growth factor I polypeptide. In other embodiments, the alpha-1 proteinase inhibitor contains glutamine for methionine at amino acid residue 351 and leucine for methionine at amino acid residue 358. In still other embodiments, the alpha-1 proteinase inhibitor encompasses the carboxy-terminal 26 amino acid residues of the inhibitor.

BRIEF DESCRIPTION OF THE DRAWINGS

FIG. 1 shows the wound reduction effects of an IGF I-API chimera, API and C26 on kidney epithelial cells (FIG. 1A), human skin fibroblast cells (FIG. 1B), and human skin keratinocytes (FIG. 1C).

FIG. 2 shows the effects of an IGF I-API chimera, API and C26 on proliferation of kidney epithelial cells (FIG. 2A), human skin fibroblast cells (FIG. 2B), and human skin keratinocytes (FIG. 2C).

FIG. 3 shows the effect of C26 peptide (closed squares) as a growth factor on human skin keratinocytes (FIG. 3A) and hepatoma cells Hep G2 (FIG. 3B) compared to EGF (open circles). Open squares represent the oxidized form C26.

FIG. 4 shows the effect of the IGF 1-API chimera on skin wounds of normal (FIG. 4A) and diabetic (FIG. 4B) mice.

DETAILED DESCRIPTION OF THE INVENTION

Figure 1A:
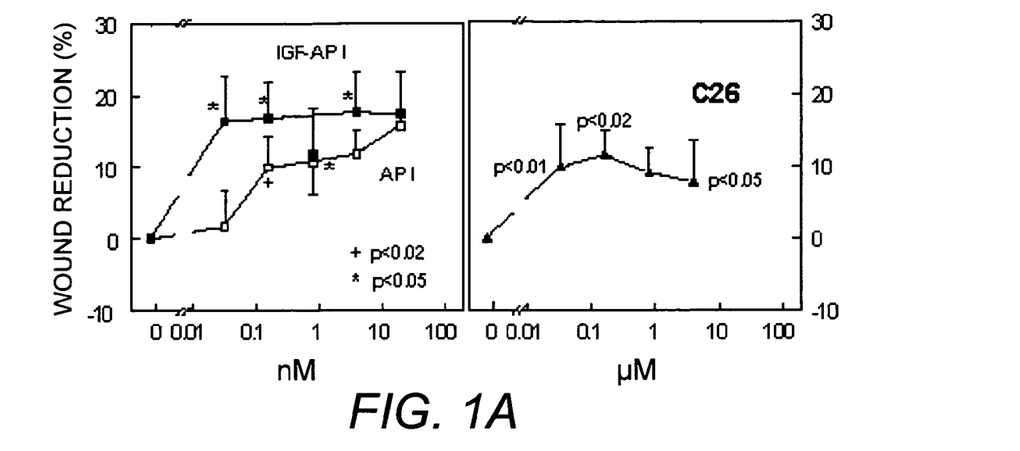

It has now been found that portions of API (e.g., the carboxy-terminal 26 amino acid residues of API) and IGF-API chimeras are effective agents for use in wound repair which are comparable or surpass the action of API alone. Natural API, IGF-API and C26 proteins were studied for their effect on wound reduction using porcine kidney epithelial cells, an experimental system for repair of injuries typical of acute renal failure (Sponsel, et al. (1994) *Am. J. Physiol.* 267(2 Pt 2):F257-64). All agents significantly increased wound healing (FIG. 1A). The most effective compound was IGF-API, which was effective at concentrations lower than 0.1 nM. The effects of API and C26 were equivalent, although C26 was active at a higher concentration (32 nM) than API (0.16 nM). However, a concentration of 32 nM is highly relevant because the physiological concentration of API is 20 μM. At sites of injury, proteolytic cleavage of API could produce micromolar concentrations of C36, the physiological equivalent of C26.

Figure 1B:
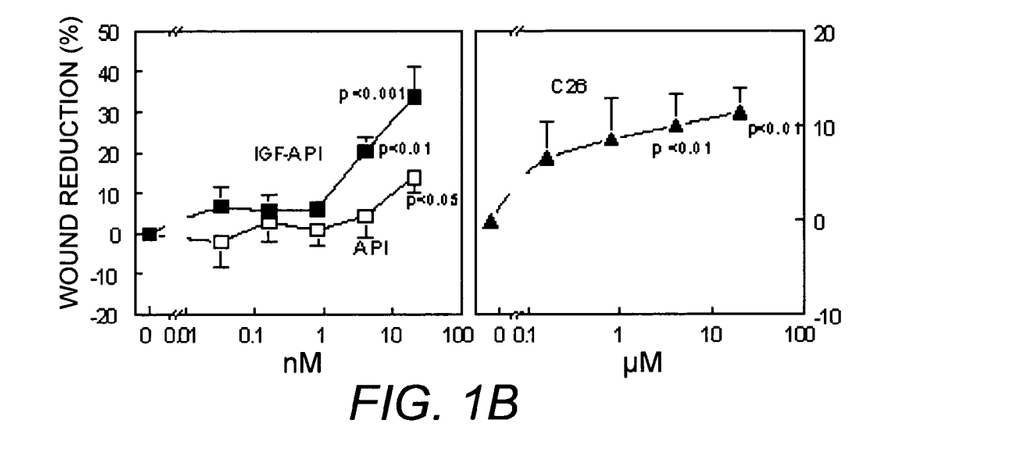

In human skin fibroblasts (FIG. 1B), IGF-API was the most active compound in wound reduction. The effects of API (20 nM) and C26 (8 μM) were significant, but lower than the effects obtained with IGF-API (8-20 nM).

Figure 1C:
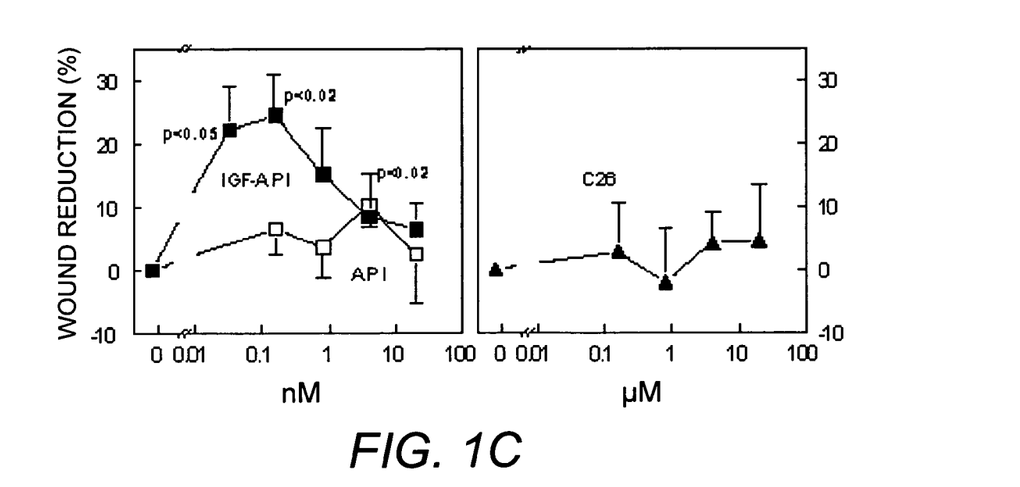

In human skin keratinocytes (FIG. 1C), IGF-API was the most active compound, even at concentrations lower than 0.1 nM. API had a marginal, but significant effect at 8 nM, where there was no significant effect of C26 in these cells. In the context of wound healing in vivo, these results indicate that the provisional closure mediated by skin fibroblasts is facilitated by IGF-API, API and C26 with IGF-API being the most active compound. IGF-API would also be useful during the second phase of wound healing, involving the regeneration of the keratinocyte layer.

Figure 2A:
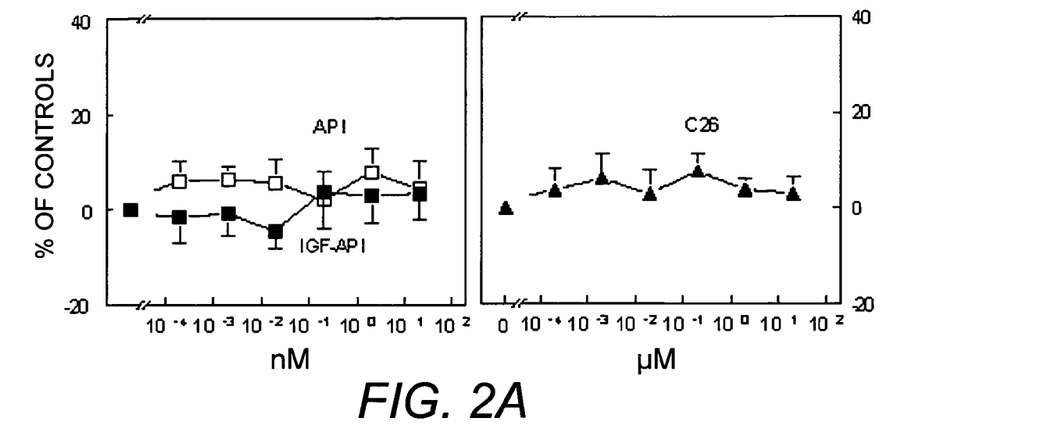
Figure 2B:
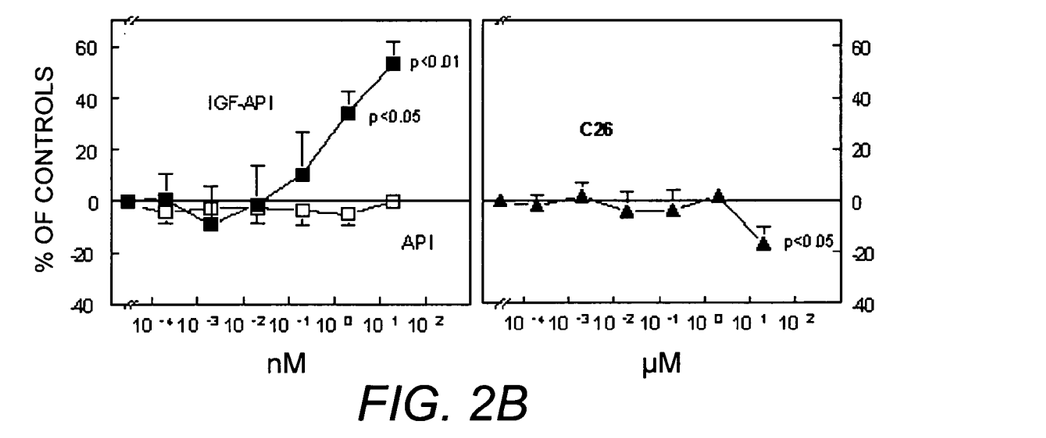
Figure 2C:
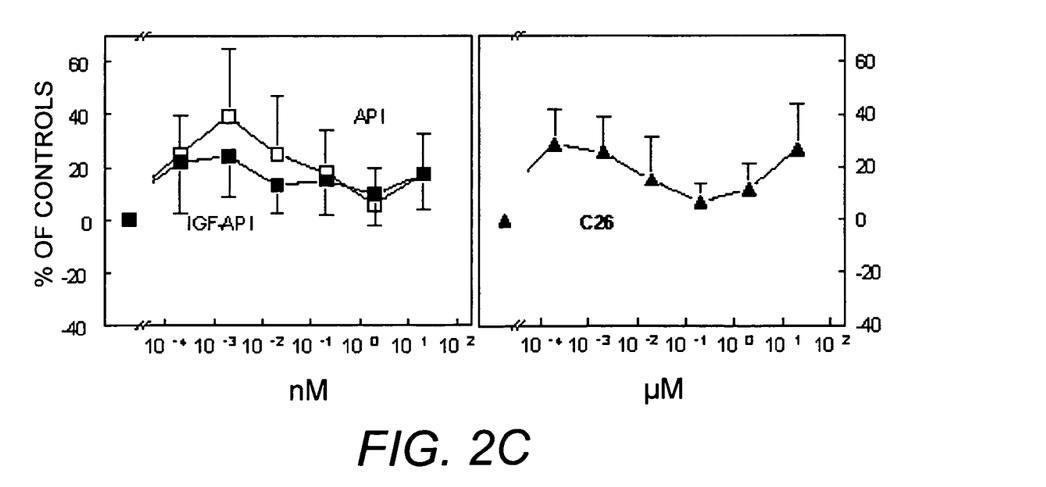

Because the in vitro wound healing experiments disclosed above are irrespective of the mechanisms involved, it was determined what effect IGF-API, API and C26 have on cell proliferation. Cell proliferation was analyzed using the well-established Alamar blue technique developed for hematopoietic cells and endothelial cells (DiFalco, et al. (1997) *Biochem. J.* 326:407-13; DiFalco & Congote (2002) *Cytokine* 18(1):51-60; Sandoval, et al. (2002) supra). As far as kidney epithelial cells and keratinocytes are concerned, there was no significant stimulation of cell proliferation with any of the agents tested (FIGS. 2A and 2C, respectively). Only IGF-API caused a significance increase in cell proliferation of human skin fibroblast cultures, indicating that cell proliferation was one of the components for improved wound healing with these cells (FIG. 2B). For all other cells studied, a mechanism independent of cell proliferation (e.g., cell migration) was probably responsible for wound closure. Accordingly, while C26 appears to be an effective wound healing agent in the first stages of wound healing, (i.e., involving closure mediated by skin fibroblasts), IGF-API is effective at all stages of wound healing, including the final repair of the keratinocyte layer.

Figure 3A:
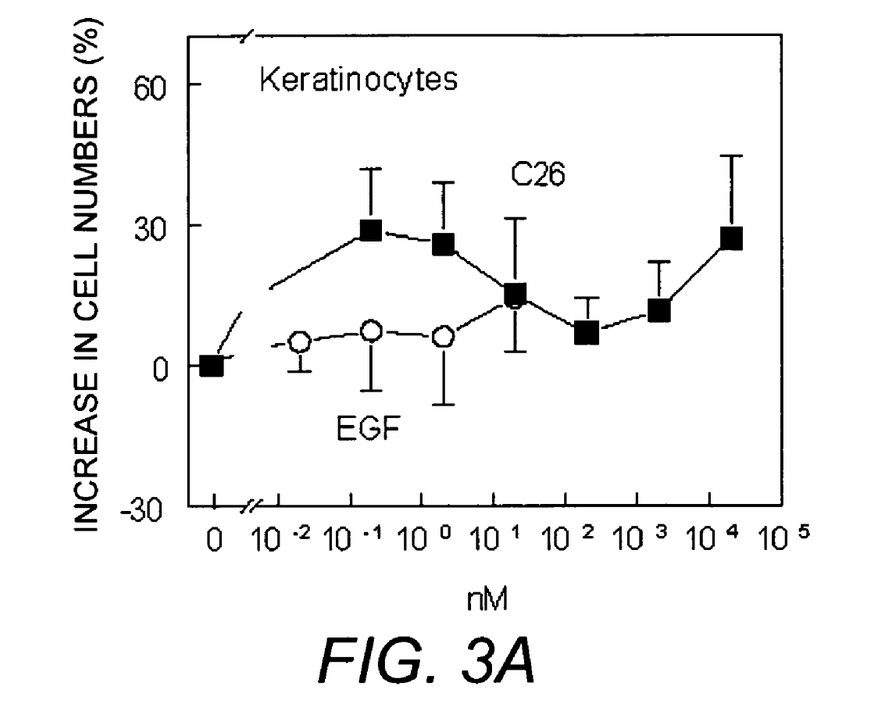
Figure 3B:
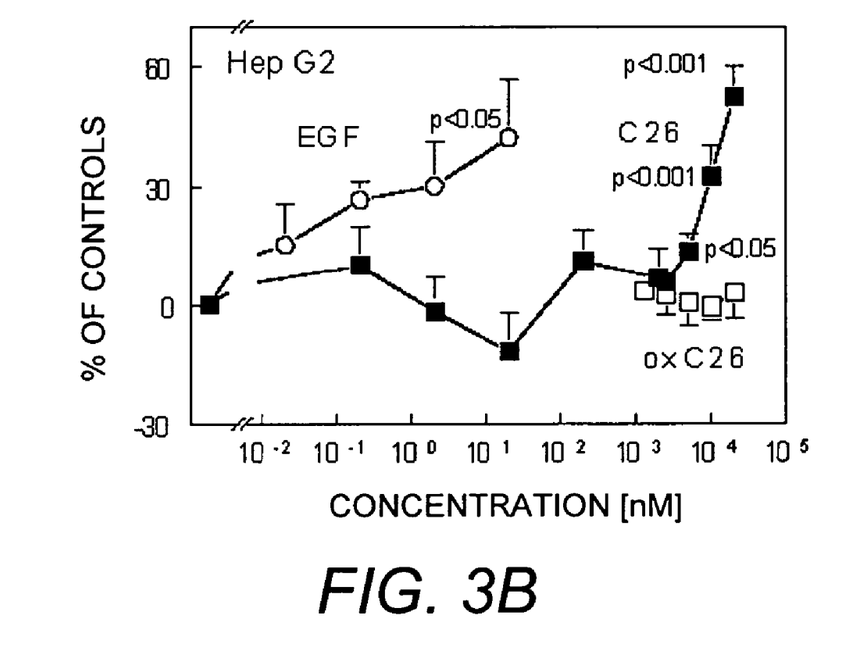

While C26 marginally stimulated cell proliferation in any of the cell studied (FIG. 2), the effect of C26 on keratinocyte cell proliferation was nonetheless higher than the effects of equivalent concentrations of epidermal growth factor (EGF) (FIG. 3A). Furthermore, C26 (20 μM) significantly increased cell proliferation in the hepatoma cell line Hep G2 (FIG. 3B). This is the first time that the C-terminal section of API has been implicated in cell proliferation. As such, API may play a role in the survival or regeneration of hepatocytes in cases of API deficiency. It has been found that API has growth promoting activities in several hematopoietic, epithelial and fibroblast cell lines (Crisp, et al. (2000) *J. Biol. Chem.* 275 (26):19628-37; Sandoval, et al. (2003) supra; Schwede, et al. (2003) supra; Dabbagh, et al. (2001) *J. Cell Physiol.* 186:73-81). However, the localization of the growth promoting activity for hepatocytes at the C-terminal end of API was unexpected. This effect was completely eliminated when the methionines of C26 were oxidized with performic acid (FIG. 3B, open squares). In view of these results, C26 is useful in methods of stimulating hepatocyte cell proliferation and may be useful in the treatment of many diseases involving hepatic injury and regeneration. The absence of this peptide in patients with API deficiency could contribute to the pathogenesis of liver function, in particular in those patients with combined API deficiency and liver dysfunctions such as cirrhosis or hepatitis.

Figure 4A:
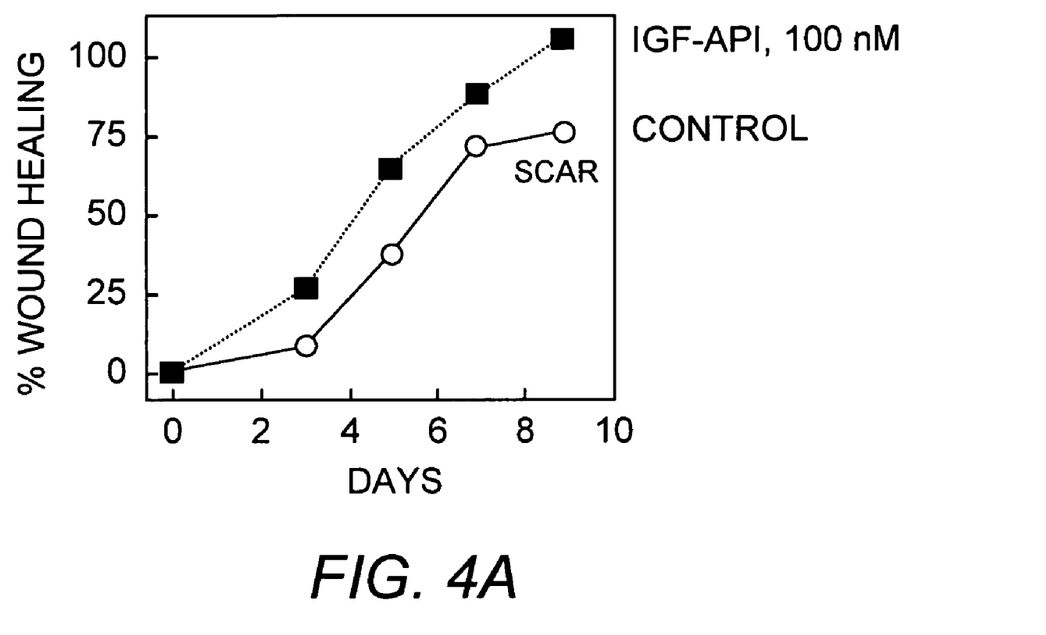
Figure 4B:
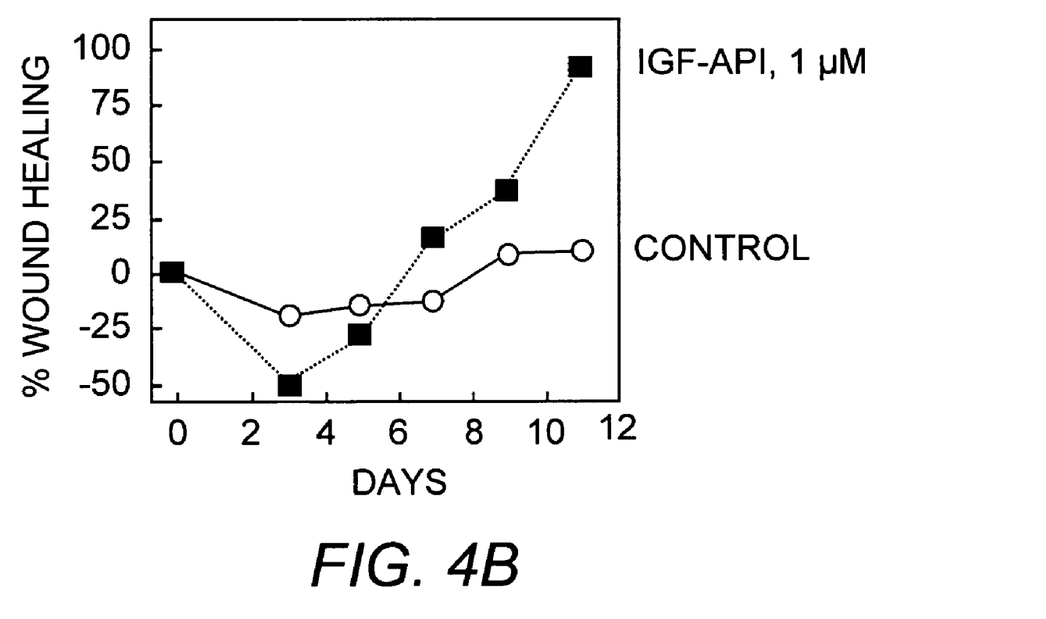

To further evaluate the efficacy of the instant IGF-API chimeric protein, wound healing in normal and diabetic mice was analysed; normal mice are a model for acute wound healing, whereas diabetic mice are an experimental model for impaired, chronic wounds. In the genetic diabetic mouse model, wound healing operates by granulation tissue formation and re-epithelialization rather than by contraction (Grinnell & Zhu (1994) supra). FIG. 4A shows wound healing in a normal mouse treated with 100 nM IGF-API in phosphate-buffered saline (PBS) during the first 5 days after wounding. The control wound received the vehicle alone (PBS). FIG. 4B shows wound healing in a diabetic mouse treated with 1 μM IGF-API at days 0, 1, 2, 3 and 5 days after wounding. The control wound received the vehicle alone (PBS). The % closure of the wounds was measured as indicated herein. In both cases there was an improvement in wound healing. The initial decrease in wound healing observed in the diabetic mouse is typical of this model and may be accentuated in the presence of IGF-API due to the chemotactic and mitogenic activities towards neutrophil/macrophages. The results shown in FIG. 4 clearly indicate that IGF-API facilitates wound healing in vivo and is useful in the healing of chronic and acute wounds.

Accordingly, the present invention relates a method for stimulating wound healing (either chronic or acute) in a patient by administering an effective amount of at least a portion of an alpha-1 proteinase inhibitor or a chimeric protein thereof. An effective amount refers to an amount effective, at dosages and for periods of time necessary, to achieve the desired therapeutic result, such as a 10%, 20%, 30%, 40%, 50% or more increase in the % closure of the wound as compared to a wound which has not been treated with agent. Wound healing can be monitored, e.g., based upon visual observation. A therapeutically effective amount of an alpha-1 proteinase inhibitor or chimera thereof may vary according to factors such as the disease state, age, sex, and weight of the individual. Dosage regimens can be adjusted to provide the optimum therapeutic response. A therapeutically effective amount is also one in which any toxic or detrimental effects of the agent are outweighed by the therapeutically beneficial effects.

The API protein, peptide, or chimeric molecules of the present invention can be administered as part of a pharmaceutical composition. Such a pharmaceutical composition can include any standard physiologically and/or pharmaceutically acceptable carrier known in the art (e.g., liposomes/cationic lipids/creams). See Remington: The Science and Practice of Pharmacy, Alfonso R. Gennaro, editor, 20th ed. Lippincott Williams & Wilkins: Philadelphia, Pa., 2000. The compositions should be sterile and contain a therapeutically effective amount of therapeutic agent in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism.

The API protein, peptide, or chimera molecules can be administered via a variety of routes including, but not limited to topical, transdermal, oral, subcutaneous and the like via standard medical practices. Topical application by use of creams, lotions, and the like are particular desirable for skin repair.

The API proteins of the instant invention (i.e., IGF-API chimera or portions of API, e.g., C26) can be administered alone or admixed together with a suitably acceptable carrier to provide even greater wound healing properties. Moreover, the API protein, peptide, or chimera molecules of this invention can be combined with other known growth factors to provide further synergistic wound healing properties.

An API protein, peptide, or chimera of the invention can be used alone or in combination with other agents for the manufacture of a medicament for use in the treatment of wounds of an animal, preferably a human. Alternatively, a portion of an alpha-1 proteinase inhibitor can be used for treating a disease or condition associated with the liver. In accordance with such treatment, an effective amount of at least a portion of an alpha-1 proteinase inhibitor is administered to an animal or human patient so that a disease or condition associated with the liver is treated. Subjects who could benefit from such treatment include those with liver diseases or conditions including, but not limited to, API deficiency combined with liver dysfunctions such as cirrhosis or hepatitis.

One embodiment of the instant invention embraces at least a portion of an alpha-1 proteinase inhibitor. As used in the context of the instant invention, at least a portion of an alpha-1 protease inhibitor is intended to mean at least a 26, 36, 46, 56, 100, 150, 200, or more amino acid residue fragment of the full-length alpha-1 protease inhibitor, set forth herein as SEQ ID NO:1. In certain embodiments, the portion of an alpha-1 protease inhibitor is the C-terminal portion of SEQ ID NO:1. In particular embodiments, a portion of an alpha-1 protease inhibitor is the carboxy-terminal 26 amino acid residues of SEQ ID NO:1, set forth herein as SEQ ID NO:2.

API peptides and proteins disclosed herein can be modified by deletion, substitution or addition of at least one amino acid residue of the sequence. A modified or variant polypeptide and reference polypeptide may differ in amino acid sequence by one or more substitutions, additions, deletions, truncations which may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and asparatic acid; c) asparagine and glutamine d) arginine and lysine; e) isoleucine, leucine, methionine and valine and f) phenylalanine, tyrosine and tryptophan. Desirably a variant retains the same biological function and activity as the reference polypeptide from which it varies.

A functionally equivalent polypeptide according to the invention is a variant wherein one or more amino acid residues are substituted with conserved amino acid residues, or one in which one or more amino acid residues includes a substituent group. Conservative substitutions are the replacements, one for another, among the aliphatic amino acids Ala, Val, Leu and Ile; interchange of the hydroxl residues Ser and Thr; exchange of the acidic residues Asp and Glu; substitution between amide residues Asn and Gln; exchange of the basic residues Lys and Arg; and replacements among aromatic residues Phe and Tyr.

In addition, the invention embraces polypeptide sequences having at least 75% identity with the polypeptide sequences as herein disclosed, or fragments and functionally equivalent polypeptides thereof. In one embodiment, the polypeptides have at least 85% identity, more preferably at least 90% identity, even more preferably at least 95% identity, still more preferably at least 97% identity, and most preferably at least 99% identity with the amino acid sequences illustrated herein. A functionally equivalent alpha-1 proteinase inhibitor particularly embraced by the instant invention contains a glutamine residue substituted for the methionine residue located at amino acid residue 351 of SEQ ID NO:1; and a leucine residue substituted for the methionine at amino acid residue 358 of SEQ ID NO:1.

It will be apparent to one skilled in the art that modified amino acids include, by way of example and not by way of limitation, 4-hydroxyproline, 5-hydroxylysine, $N^6$-acetyllysine, $N^6$-methyllysine, $N^6,N^6$-dimethyllysine, $N^6,N^6,N^6$-trimethyllysine, cyclohexyalanine, D-amino acids, ornithine. Other modifications include amino acids with a $C_2$, $C_3$ or $C_4$ alkyl R group optionally substituted by 1, 2 or 3 substituents selected from halo (e.g., F, Br, I), hydroxy or $C_1$-$C_4$ alkoxy. Alternatively, a protein of the instant invention is modified by acetylation and/or amidation.

Optionally, the polypeptides or peptides of the invention are modified by cyclization. Cyclization is known in the art. See Scott, et al. (2001) Chem. Biol. 8:801-815; Gellerman, et al. (2001) J. Peptide Res. 57:277-291; Dutta, et al. (2000) J. Peptide Res. 8:398-412; Ngoka and Gross (1999) J. Amer. Soc. Mass Spec. 10:360-363.

Fusion proteins are also embraced by the instant invention. As exemplified herein, an IGF-API chimeric protein was highly effective in stimulating wound healing in vitro and in vivo. Accordingly, a particular embodiment of the instant invention is a chimeric protein composed of at least a portion of API operatively linked to at least a portion of an insulin-like growth factor I (IGF I) polypeptide. As used herein, fused or operably linked is intended to mean that the API protein and IGF protein are joined by peptide bonds to create a contiguous protein sequence. As part of the fusion protein, API can be located on the C-terminus or N-terminus. In certain embodiments, the proteins are directly fused to one another. In other embodiments, the API and IGF proteins are fused via a short linker sequence, e.g., a poly glycine linker or glycine-cysteine linker. Linkers and use thereof are well-known to those of skill in the art. An exemplary IGF-API fusion protein is set forth herein as SEQ ID NO:3.

A portion of an IGF I protein is intended to encompass a 40, 50, 60, 65, 70, 75 or 80 amino acid residue fragment of the full-length precursor IGF I, set forth herein as SEQ ID NO:4. In certain embodiments, the portion selected retains wound healing activity. In particular embodiments, the IGF I portion is a mature IGF I protein (i.e., with no signal sequence attached). As exemplified herein, a portion of IGF I encompasses amino acid residues 51 to 118 of the full-length precursor IGF I protein of SEQ ID NO:4, a sequence set forth herein as SEQ ID NO:5.

Like IGF I, platelet-derived growth factor (PDGF), epidermal growth factor (EGF), basic fibroblast growth factor (bFGF), and transforming growth factor-beta (TGF-bet) exhibit the ability to accelerate wound healing (Loot, et al. (2002) supra). Accordingly, it is contemplated that fusion proteins composed of any one of a variety of growth factors operatively linked with at least a portion of API will stimulate wound healing in accordance with the instant method.

Proteins or peptides of the instant invention can be produced by recombinant DNA technology or chemically synthesized, or produced by a combination thereof. A protein composition produced by recombinant DNA technology is generally expressed from a nucleic acid encoding the protein. Such a nucleic acid can be isolated by convention methodologies such as restriction enzyme-based cloning. For example, DNA fragments coding for the different protein or peptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. Alternatively, the isolated nucleic acid molecule can be synthesized by conventional techniques including automated DNA synthesis or polymerase chain reaction (PCR) amplification. PCR amplification of gene fragments can be carried out using anchor primers which give rise to complementary overhangs between two consecutive gene fragments which are subsequently annealed and reamplified to generate a chimeric gene sequence (see, e.g., Current Protocols in Molecular Biology, eds. Ausubel, et al. John Wiley & Sons, 1992).

Recombinant production of a desired protein typically involves directly expressing the desired protein from a recombinant expression vector or expressing the desired protein with a heterologous protein sequence such as a tag or a signal sequence to facilitate purification or secretion of the desired protein from a host cell. In certain host cells (e.g., mammalian host cells), expression and/or secretion of a desired protein can be increased through use of a heterologous signal sequence. Such tags include, but are not limited to a his-tag or FLAG®-tag.

A recombinant expression vector generally harbors nucleic acids encoding the desired protein in a form suitable for expression, i.e., the recombinant expression vector includes one or more regulatory sequences operatively-linked to the nucleic acid to be expressed. Expression vector and recombinant expression vector are used interchangeably herein, and in the context of a recombinant expression vector, operatively-linked is intended to mean that the nucleic acid of interest is linked to the regulatory sequence(s) in a manner which allows for expression of the nucleic acid (e.g., in an in vitro transcription/translation system or in a host cell). A regulatory sequence is intended to include promoters, enhancers and other expression control elements (e.g., polyadenylation signals). Such regulatory sequences are described, for example, in Goeddel (1990) *Methods Enzymol.* 185:3-7. Regulatory sequences include those which direct constitutive expression of a nucleic acid in many types of host cells and those which direct expression of the nucleic acid only in certain host cells (e.g., tissue-specific regulatory sequences). It will be appreciated by one of skill in the art that the design of the expression vector depends on such factors as the choice of the host cell to be transformed, the level of expression of the desired protein, and the like.

A recombinant expression vector can be designed for expression of a desired protein in prokaryotic or eukaryotic cells. For example, a protein composition of the instant invention can be expressed in bacterial cells such as *E. coli*, insect cells (using baculovirus expression vectors), yeast cells or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Examples of suitable inducible *E. coli* expression vectors include pTrc (Amann, et al. (1988) *Gene* 69:301-315) and pET ld (Studier, et al. (1990) *Methods Enzymol.* 185:60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

A yeast expression vector also encompassed within the scope of the invention. Examples of vectors for expression in yeast such as *Saccharomyces cerevisiae* include pYepSec 1 (Baldari, et al. (1987) *EMBO J.* 6:229-234), pMFa (Kurjan and Herskowitz (1982) *Cell* 30:933-943), pJRY88 (Schultz, et al. (1987) *Gene* 54:113-123), pYES2 (INVITROGEN™ Corp., San Diego, Calif.), and picZ (INVITROGEN™ Corp., San Diego, Calif.).

Alternatively, a protein composition of the invention can be expressed in insect cells as exemplified herein using baculovirus expression vectors. Baculovirus vectors available for expression of proteins in cultured insect cells (e.g., Sf9 cells) include the pAc series (Smith, et al. (1983) *Mol. Cell Biol.* 3:2156-2165) and the pVL series (Lucklow and Summers (1989) *Virology* 170:31-39) of vectors.

Recombinant expression vectors in which the nucleic acid of interest is homologously recombined into a specific site of the host cell's genome are also contemplated. The terms host cell and recombinant host cell are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Expression vector DNA can be introduced into prokaryotic or eukaryotic cells via conventional transformation or transfection techniques. As used herein, the terms transformation and transfection are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (1989) supra, and other laboratory manuals.

To identify and select transformed or transfected host cells, a gene that encodes a selectable marker (e.g., resistance to antibiotics) is generally introduced into the host cells along with the nucleic acid of interest. Suitable selectable markers include those which confer resistance to drugs, such as G418, hygromycin and methotrexate. Nucleic acids encoding a selectable marker can be introduced into a host cell on the same vector as that encoding the protein of interest or can be introduced on a separate vector. Cells stably transformed or transfected with the introduced nucleic acid can be identified by drug selection (e.g., cells that have incorporated the selectable marker gene will survive, while the other cells die).

Once produced, the desired protein or peptide is either recovered as a secreted protein or from host cell lysates, when directly expressed without a secretory signal. Purification of the protein composition from recombinant cell proteins can be carried out by centrifuging the culture medium or lysate to remove particulate cell debris and purifying the protein composition by, e.g., fractionation on immunoaffinity or ion-exchange columns, ethanol precipitation, chitin column chromatography, reverse phase HPLC, chromatography on silica or on a anion-exchange resin such as DEAE, chromatofocusing, SDS-PAGE, ammonium sulfate precipitation, gel filtration, or ligand affinity chromatography (e.g., $Ni^{2+}$-agarose chromatography).

In addition to recombinant production, the protein composition can be produced by direct peptide synthesis using solid-phase techniques (Merrifield (1963) *J. Am. Chem. Soc.* 85:2149-2154). Protein synthesis can be performed using manual techniques or by automation. Automated synthesis can be achieved, for example, using Applied Biosystems 431A Peptide Synthesizer (Perkin Elmer, Boston, Mass.). Various fragments of the protein composition can be chemically-synthesized separately and combined using chemical methods to produce the full-length molecule. A number of cross-linkers are well-known in the art, including homo- or hetero-bifunctional cross-linkers, such as BMH, SPDP, etc. Chemical methods for cross-linking molecules to the amino- or carboxy-terminus of a protein are reviewed by Offord (1992) In: Protein Engineering-A Practical Approach, Rees, et al., eds., Oxford University Press.

The invention is described in greater detail by the following non-limiting examples.

EXAMPLE 1

Recombinant Protein Production

Recombinant proteins expressed herein included the C-terminal 26 amino acid residues of API (SEQ ID NO:2), API itself, and an IGF I-API fusion protein (SEQ ID NO:3). The IGF I-API fusion protein was derived by inserting the API sequence into the a synthetic bombyxin-IGF 1 fusion protein construct known as BIGFI (GenBank Accession No. AY380807; Sandoval, et al. (2003) *Biochem. Pharmacol.* 65:2055-2063). Accordingly, with reference to SEQ ID NO:3, amino acids 7-74 are identical to human IGF-I (i.e., amino acid residues 51 to 118 as found in GenBank Accession No. X00173); amino acids 75-87 of are a flexible poly-glycine linker; amino acid residues 88-91 correspond to amino acids encoded by the multiple cloning site of BIGFI; amino acids 92-485 encompass the amino acid sequence of API (see, e.g., Zhu, et al. (1987) *Biochem. J.* 246:25-36); amino acid residues 442 and 449 correspond to positions 351 and 358 of API, wherein the methionines of the active site were mutated to Glu (442) and Lys (449), respectively; amino acid residues 486-488 correspond to amino acids encoded by the multiple cloning site of BIGFI; and amino acids 489 to 494 constitute a hexa-histidine tag from BIGFI.

Both classical baculovirus and non-lytic insect cell expression systems result in the secretion of properly folded, bifunctional chimeras in yields which surpass the expression of the single components (Curtis, et al. (2002) *J. Biotechnol.* 93(1): 35-44; Sandoval, et al. (2003) supra). Thus, an insect-based expression system was employed herein in accordance with standard practices (see, Sandoval, et al. (2003) supra). Using such a system, milligram amounts of IGF-API were obtained from supernatants of insect cell cultures. It is known that IGFI is a better mitogen than IGF II, and therefore IGF I was selected for the analysis carried out in the instant invention. Advantageously, API mutated at Met351 and Met358 of the active site (i.e., Met351Glu and Met358Lys) improved production in insect cell culture and was contemplated to prevent inactivation by oxidation.

C26 (SEQ ID NO:2) is a small peptide corresponding to the last 26 amino acids of API. After proteolytic cleavage of API in vivo, a fragment of 36 amino acids is obtained (C36). C26 conserves the five amino acids Phe-Val-Phe-Leu-Met (SEQ ID NO:6) known to be required for binding to the putative serpin-enzyme complex receptor (Crisp, et al. (2000) supra). Furthermore, C26 contains all the elements required for the beta-sheet conformation of the natural peptide. The 3D structures of BIGFI and C26 were estimated using the internet-based Swiss Model program found at expasy.org at the worldwide web (Guex & Peitsch (1997) *Electrophoresis* 18(15): 2714-23; Peitsch, et al. (1995) *Trends Biochem. Sci.* 20(2): 82-4-82-4; Schwede, et al. (2003) *Nucleic Acids Res.* 31(13): 3381-5).

EXAMPLE 2

An In Vitro Model of Wound Healing

Wound healing was measured using an art-established monolayer cell culture method (Nwomeh, et al. (1998) supra). Cells to be studied were plated in 48-well tissue culture plates at a cell density appropriate for obtaining confluent monolayers after one day in culture. Circular wounds were made in the center of the wells by placing a siliconized 200 μL tip into the well and lifting the cells from the plastic by applying suction. The successful creation of wounds was analysed using a phase contrast microscope. Cells were subsequently treated with control media or media containing the factors to be tested. The size of the wounds was immediately recorded for each well. The wounds were large enough to allow for a long-term incubation thereby improving the accuracy of the determinations. After one or two days in culture (depending on the cells studied), the size of the wounds was measured again. Wound dimensions were evaluated with a Leica MZFL11 stereo microscope. Computer images of the wounds were recorded with imaging software and contours of each wound before and after treatment were traced manually. Collections of contours for all wounds were converted to BMP files and quantitated using the Band-Leader program. The results were expressed as % reduction of wounds taking as 100% the reduction obtained in control cell cultures. No change corresponded to 0%, whereas complete closure corresponded to 100%. This system works well with close monitoring of cell densities. To prevent excess cell growth, the incubations were performed in serum-free medium supplemented with a single protein, transferrin (5 μg/mL). The absence of serum slowed down the healing process (one day in LLC-PK1 cells, two days in all other cultures), but reflected more accurately the situation likely to prevail in topical applications in vivo. Wound closure depends on the migration of cells at the sites of the wound and on cell proliferation. In these experiments, wound closure was being analysed, independent of the mechanism involved.

Cells analysed in the in vitro assay disclosed herein included monolayers of LLC-PK1 cells, a porcine kidney epithelial cell line used as an experimental system of wound healing for acute renal failure (Sponsel, et al. (1994) supra); monolayers of primary human skin fibroblasts; and monolayers of human skin keratinocytes. It was found that keratinocytes were so firmly attached to the culture surface that the vacuum suction was not powerful enough to produce complete circular wounds. This made measurements of keratinocyte wound closure particularly difficult and time consuming. According, wound closure measurements of a cross created with two perpendicular cell lesions was particularly effective for analysing human skin keratinocytes (Sponsel, et al. (1994) supra).

EXAMPLE 3

Cell Proliferation Assays

The effects of IGF-API, API and C26 on cell proliferation were also evaluated using the art-established Alamar blue technique developed for hematopoietic cells or endothelial cells (DiFalco, et al. (1997) *Biochem. J.* 326:407-13; DiFalco & Congote (2002) *Cytokine* 18 (1):51-60; Sandoval, et al. (2002) supra). Five thousand cells per well were plated in 96-well plates and grown over night in complete cell culture medium. The cells were subsequently starved for one day in serum-free medium supplemented with 5 µg/mL bovine transferrin and 200 µg/mL fatty-acid free, tissue culture-tested, bovine serum albumin and incubated for two days in the presence of the API derivatives indicated. For experiments with the hepatoma cell line, Hep G2, only 3000 cells were plated per well.

Cell proliferation with EGF and C26 was also analysed for keratinocytes and Hep G2 cells. The number of experiments using keratinocytes with EGF was five, and 10 to 11 with C26. The number of experiments using Hep G2 with EGF and C26 was five, except for 20 nM EGF (n=8, P<0.05, paired t-test) and for 20 µM C26 (n=21, p<0.001, paired t-test and Student-Newman-Keuls test). All other P values were according to the Student-Newman-Keul multiple comparisons test.

EXAMPLE 4

In Vivo Efficacy of IGF-API on Skin Wounds

The methodology for the preclinical studies was based on procedures described in similar experiments by Brown, et al. ((1994) *J. Surg. Res.* 56(6):562-70). Normal adult female C57BL/6 mice or C57BL/KsJ-db/db genetically diabetic mice (Jackson Laboratories, West Grove, Pa.) were anaesthetized with Ketamine-Xylazine-Acetopromazine. The backs were shaved, washed with povidone-iodine solution and wiped with sterile water. Two 1-cm$^2$ full thickness wounds were created on the back. After wounding, Tincture Benzoin compound was applied to the edges of the wounds. A semi-permeable, transparent polyurethane dressing (OPSITE®) was placed over the wound and the edges were sealed with the benzoin. At the time of wounding, the healing factors were applied once daily for the first 5 days or at days 0, 1, 2, 3 and 5. IGF-API was dissolved in sterile phosphate-buffered saline (PBS) at the doses indicated in FIG. 4 and 50 µL of the solutions were applied with a 30-gauge needle beneath the OPSITE®) dressing. The liquid was allowed to spread over the wound. The control wound received 50 µL of PBS alone. The edges of epithelial migration were serially traced onto household plastic wrap at days 0, 3, 7, 9 or 11 and the areas of the traced wounds were scanned and measured with an imaging program (measurements of wound closure).

---

What is claimed is:

1. A pharmaceutical composition comprising the C-terminal portion of an alpha-1 proteinase inhibitor, wherein said portion consists of SEQ ID NO:2, and a pharmaceutically acceptable carrier.

2. The pharmaceutical composition of claim 1, further comprising at least a portion of an insulin-like growth factor I polypeptide linked to the portion of the alpha-1 proteinase inhibitor, wherein said portion of the insulin-like growth factor I polypeptide includes the amino acid sequence set forth in SEQ ID NO:5.

3. A method for stimulating wound healing comprising administering an effective amount of the carboxy-terminal portion of alpha-1 proteinase inhibitor, wherein said portion consists of SEQ ID NO:2, so that wound healing is stimulated.

4. The method of claim 3, further comprising at least a portion of an insulin-like growth factor I polypeptide linked to the portion of the alpha-1 proteinase inhibitor, wherein said portion of the insulin-like growth factor I polypeptide includes the amino acid sequence set forth in SEQ ID NO:5.

* * * * *

SEQUENCE LISTING

```
<160> NUMBER OF SEQ ID NOS: 6

<210> SEQ ID NO 1
<211> LENGTH: 394
<212> TYPE: PRT
<213> ORGANISM: Homo Sapiens

<400> SEQUENCE: 1

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110
```

```
Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
        210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
        260                 265                 270

Thr Lys Phe Leu Glu Asn Glu Asp Arg Arg Ser Ala Ser Leu His Leu
    275                 280                 285

Pro Lys Leu Ser Ile Thr Gly Thr Tyr Asp Leu Lys Ser Val Leu Gly
        290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Glu Phe
            340                 345                 350

Leu Glu Ala Ile Pro Leu Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 2
<211> LENGTH: 26
<212> TYPE: PRT
<213> ORGANISM: Artificial Sequence
<220> FEATURE:
<223> OTHER INFORMATION: Synthetic peptide

<400> SEQUENCE: 2

Pro Phe Val Phe Leu Met Ile Glu Gln Asn Thr Lys Ser Pro Leu Phe
1               5                   10                  15

Met Gly Lys Val Val Asn Pro Thr Gln Lys
            20                  25

<210> SEQ ID NO 3
<211> LENGTH: 494
<212> TYPE: PRT
<213> ORGANISM: Artificial Sequence
<220> FEATURE:
<223> OTHER INFORMATION: Synthetic fusion protein
```

<400> SEQUENCE: 3

```
Asn Gln Pro Gln Met Val Glu Thr Leu Cys Gly Ala Glu Leu Val Asp
1               5                   10                  15

Ala Leu Gln Phe Val Cys Gly Asp Arg Gly Phe Tyr Phe Asn Lys Pro
            20                  25                  30

Thr Gly Tyr Gly Ser Ser Arg Arg Ala Pro Gln Thr Gly Ile Val
        35                  40                  45

Asp Glu Cys Cys Phe Arg Ser Cys Asp Leu Arg Arg Leu Glu Met Tyr
    50                  55                  60

Cys Ala Pro Leu Lys Pro Ala Lys Ser Ala Gly Gly Ser Gly Gly
65                  70                  75                  80

Gly Gly Gly Gly Gly Gly His Gly Leu Ala Glu Asp Pro Gln Gly
                85                  90                  95

Asp Ala Ala Gln Lys Thr Asp Thr Ser His His Asp Gln Asp His Pro
            100                 105                 110

Thr Phe Asn Lys Ile Thr Pro Asn Leu Ala Glu Phe Ala Phe Ser Leu
            115                 120                 125

Tyr Arg Gln Leu Ala His Gln Ser Asn Ser Thr Asn Ile Phe Phe Ser
130                 135                 140

Pro Val Ser Ile Ala Thr Ala Phe Ala Met Leu Ser Leu Gly Thr Lys
145                 150                 155                 160

Ala Asp Thr His Asp Glu Ile Leu Glu Gly Leu Asn Phe Asn Leu Thr
                165                 170                 175

Glu Ile Pro Glu Ala Gln Ile His Glu Gly Phe Gln Glu Leu Leu Arg
            180                 185                 190

Thr Leu Asn Gln Pro Asp Ser Gln Leu Gln Leu Thr Thr Gly Asn Gly
            195                 200                 205

Leu Phe Leu Ser Glu Gly Leu Lys Leu Val Asp Lys Phe Leu Glu Asp
210                 215                 220

Val Lys Lys Leu Tyr His Ser Glu Ala Phe Thr Val Asn Phe Gly Asp
225                 230                 235                 240

Thr Glu Glu Ala Lys Lys Gln Ile Asn Asp Tyr Val Glu Lys Gly Thr
                245                 250                 255

Gln Gly Lys Ile Val Asp Leu Val Lys Glu Leu Asp Arg Asp Thr Val
            260                 265                 270

Phe Ala Leu Val Asn Tyr Ile Phe Phe Lys Gly Lys Trp Glu Arg Pro
            275                 280                 285

Phe Glu Val Lys Asp Thr Glu Glu Asp Phe His Val Asp Gln Val
        290                 295                 300

Thr Thr Val Lys Val Pro Met Met Lys Arg Leu Gly Met Phe Asn Ile
305                 310                 315                 320

Gln His Cys Lys Lys Leu Ser Ser Trp Val Leu Leu Met Lys Tyr Leu
                325                 330                 335

Gly Asn Ala Thr Ala Ile Phe Phe Leu Pro Asp Glu Gly Lys Leu Gln
            340                 345                 350

His Leu Glu Asn Glu Leu Thr His Asp Ile Ile Thr Lys Phe Leu Glu
            355                 360                 365

Asn Glu Asp Arg Arg Ser Ala Ser Leu His Leu Pro Lys Leu Ser Ile
            370                 375                 380

Thr Gly Thr Tyr Asp Leu Lys Ser Val Leu Gly Gln Leu Gly Ile Thr
385                 390                 395                 400

Lys Val Phe Ser Asn Gly Ala Asp Leu Ser Gly Val Thr Glu Glu Ala
                405                 410                 415
```

```
Pro Leu Lys Leu Ser Lys Ala Val His Lys Ala Val Leu Thr Ile Asp
        420                 425                 430

Glu Lys Gly Thr Glu Ala Ala Gly Ala Glu Phe Leu Glu Ala Ile Pro
        435                 440                 445

Leu Ser Ile Pro Pro Glu Val Lys Phe Asn Lys Pro Phe Val Phe Leu
        450                 455                 460

Met Ile Glu Gln Asn Thr Lys Ser Pro Leu Phe Met Gly Lys Val Val
465                 470                 475                 480

Asn Pro Thr Gln Lys Glu His Ala His His His His His His
                485                 490

<210> SEQ ID NO 4
<211> LENGTH: 153
<212> TYPE: PRT
<213> ORGANISM: Homo sapiens

<400> SEQUENCE: 4

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150

<210> SEQ ID NO 5
<211> LENGTH: 68
<212> TYPE: PRT
<213> ORGANISM: Artificial Sequence
<220> FEATURE:
<223> OTHER INFORMATION: Synthetic protein

<400> SEQUENCE: 5

Glu Thr Leu Cys Gly Ala Glu Leu Val Asp Ala Leu Gln Phe Val Cys
1               5                   10                  15

Gly Asp Arg Gly Phe Tyr Phe Asn Lys Pro Thr Gly Tyr Gly Ser Ser
            20                  25                  30

Ser Arg Arg Ala Pro Gln Thr Gly Ile Val Asp Glu Cys Cys Phe Arg
        35                  40                  45

Ser Cys Asp Leu Arg Arg Leu Glu Met Tyr Cys Ala Pro Leu Lys Pro
    50                  55                  60

Ala Lys Ser Ala
65
```

```
<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Phe Val Phe Leu Met
1               5
```